United States Patent [19]

Peers-Trevarton

[11] Patent Number: 4,614,395
[45] Date of Patent: Sep. 30, 1986

[54] QUICK CONNECTOR TO MEDICAL ELECTRICAL LEAD

[75] Inventor: Charles A. Peers-Trevarton, Pompano Beach, Fla.

[73] Assignee: Cordis Corporation, Miami, Fla.

[21] Appl. No.: 720,284

[22] Filed: Apr. 4, 1985

[51] Int. Cl.⁴ .............................................. H01R 11/20
[52] U.S. Cl. ..................................... 339/97 R; 29/881; 339/96
[58] Field of Search ....................... 339/95 R, 95 B, 96, 339/97 R, 224; 29/874, 876, 881

[56] References Cited

U.S. PATENT DOCUMENTS

| | | | |
|---|---|---|---|
| 1,381,779 | 6/1921 | Williams | 339/100 |
| 2,340,011 | 1/1944 | Moore et al. | 339/230 R |
| 2,940,060 | 6/1960 | Haegert | 339/100 |
| 2,959,766 | 11/1960 | Jacobsen | 339/273 |
| 3,147,057 | 9/1964 | Colussi | 339/89 |
| 3,205,472 | 9/1965 | Shannon | 339/232 |
| 3,306,970 | 2/1967 | Kowalski | 174/79 |
| 3,401,371 | 9/1968 | Hammond | 339/268 |
| 3,617,986 | 11/1971 | Becker et al. | 339/94 A |
| 3,733,578 | 5/1973 | Fouche | 339/232 |
| 3,757,789 | 9/1973 | Shanker | 339/60 R |
| 3,824,556 | 7/1974 | Berkovits et al. | 339/268 S |
| 3,976,347 | 8/1976 | Cooke, Sr. et al. | 339/96 |
| 4,257,428 | 3/1981 | Barton et al. | 128/785 |
| 4,280,511 | 7/1981 | O'Neill | 128/784 |
| 4,370,014 | 1/1983 | Bourdon | 339/97 R |
| 4,411,276 | 10/1983 | Dickhudt et al. | 128/784 |
| 4,411,277 | 10/1983 | Dickhudt | 128/784 |
| 4,437,474 | 3/1984 | Peers-Trevarton | 29/876 |
| 4,446,505 | 5/1984 | Long et al. | 339/221 R |

Primary Examiner—Gil Weidenfeld
Assistant Examiner—Paula Austin
Attorney, Agent, or Firm—Henry W. Collins; Thomas R. Vigil

[57] ABSTRACT

The quick connector includes an elastomeric sleeve, a rod slidable in the sleeve, and a tube mounted in permanent assembly with one end of the rod. The tube is split at an outer end providing a pair of jaw-like tube segments which extend in divergent relation when in an open position. Each of the segments has a series of longitudinally spaced rearwardly extending barbs. A guide wire having an axially inner end is co-axially embedded in the rod and an axially outer end of the guide wire projects axially outwardly between the diverging jaw-like tube segments. A medical electrical lead is co-axially mounted over the guide wire and between the diverging jaw-like tube segments in radially disposed relation to the barbs. The lead includes a tubular insulation sheath and a coiled conductor in the sheath. The rod and the elastomeric sleeve are axially movable relative to one another after the diverging jaw-like tube segments are moved radially inwardly into a closed position to cause the barbs carried on the thus moved segments to become embedded in the coiled conductor for locking the lead in fixed assembly with the rod.

29 Claims, 7 Drawing Figures

QUICK CONNECTOR TO MEDICAL ELECTRICAL LEAD

BACKGROUND OF THE INVENTION

1. Field of the Invention

The present invention relates to a quick connector for a neural stimulator lead or a cardiac pacing lead and more particularly to a connector which enables a surgeon to install a lead terminal assembly as a new installation or to replace an existing terminal assembly with a minimum expenditure of time and with the need of a minimum amount of ancillary equipment whereby only a cutting pliers or scissors is required.

2. Description of the Prior Art

In the past, where a lead assembly had to be replaced, a surgeon was obliged to have on hand a splicing lead with connectors, crimping pliers, cutting pliers, splicing sleeves, splicing crimps and medical adhesive. The installation steps previously practiced involved a time consuming complex procedure.

Such procedure required the cutting off of the old terminal assembly, removing insulation surrounding the coils of the lead, placing the splicing sleeve over the lead body, crimping the implanted lead to the splicing lead, placing the sleeve over the crimped area, and applying medical adhesive to both ends of the sleeve to prevent fluid penetration and to wait for the adhesive to cure.

Also, heretofore various types of sliding ferrule-type clamps have been proposed in non-analogous arts for effecting a mechanical and electrical connection between a conductor and a terminal connector.

Examples of typical prior art devices, most of which are in non-analogous arts, are disclosed in the following U.S. patents:

| U.S. Pat. No. | PATENTEE |
| --- | --- |
| 1,381,779 | Williams |
| 2,340,011 | Moore et al |
| 2,940,060 | Haegert |
| 2,959,766 | Jacobsen |
| 3,147,057 | Colussi |
| 3,205,472 | Shannon |
| 3,306,970 | Kowalski |
| 3,401,371 | Hammond |
| 3,617,986 | Becker et al |
| 3,733,578 | Fouche |
| 3,757,789 | Shanker |
| 3,824,556 | Berkovits et al |
| 4,257,428 | Barton et al |
| 4,280,511 | O'Neill |
| 4,411,276 | Dickhudt et al |
| 4,411,277 | Dickhudt |

Many of the prior art patents listed above are in non-analogous art and not prior art to the connector/terminal electrode assembly for a medical electrical lead disclosed herein.

The non-analogous prior art shows different types of sliding ferrule-type clamps. See for example the Kowalski, U.S. Pat. No. 3,306,970. The Kowalski patent does not concern itself with a quick connector for a neural stimulator lead or a cardiac pacing lead as disclosed herein.

The non-analogous prior art also discloses piercing-type connectors and one example of such a connector is shown in the non-analogous Williams, U.S. Pat. No. 1,381,779. This patent relates to a dead-end clamp for cables and again is not concerned with a quick connector for a neural stimulator lead or a cardiac pacing lead.

Most ferrule-type connectors utilize screw elements such as, for example, as are shown in the non-analogous Moore et al, U.S. Pat. No. 2,340,011. This patent specifically is concerned with a battery terminal for use with storage batteries on automotive vehicles and is not concerned with quick connectors for a neural stimulator lead or a cardiac pacing lead as herein disclosed.

Ferrule-type connectors have been proposed for known use in the pacing lead art as shown in the Shanker, U.S. Pat. No. 3,757,789. This connector is used in conjunction with a body implantable electomedical device.

Other body implantable connectors are enclosed in several of the prior art patents listed above but are of a different type than the connector herein disclosed.

As will be described in greater detail hereafter, the quick connector for a neural stimulator lead or a cardiac pacing lead of the present invention differs from the structures described above by providing a unique structure for securing a medical electrical lead and coiled conductor therein in assembly with a collapsible gripper having barbs for becoming embedded with the coiled conductor and which gripper is collapsed within an axially movable silicone rubber sleeve having a configuration that is particularly suited for being received over the gripper and which has means for inhibiting axial flow of body fluids between the sleeve and the connector components once they are encased within the sleeve.

SUMMARY OF THE INVENTION

According to the invention, there is provided a method for forming a terminal electrode assembly at the proximal end of a medical electrical lead of the type comprising a tubular sheath and a coiled conductor within the sheath, said method comprising:

providing gripping means including a jaw formation with teeth capable of piercing the sheath and of making electrical connection with the coiled conductor;

providing a sleeve made of a flexible, insulative material into which said gripping means can be pulled;

providing a terminal pin with excess length which is coupled at one end to said gripping means and which can extend through said sleeve;

placing said gripping means over the proximal end of the medical electrical lead;

folding said jaw formation into and about the proximal end of the lead;

inserting said terminal pin into and through the sleeve;

pulling said terminal pin through a major portion of said sleeve to pull said gripping means and the lead proximal end into the sleeve.

Further according to the invention there is provided a terminal electrode assembly for connecting to a proximal end of a medical electrical lead of the type comprising a tubular sheath and a coiled conductor within the sheath, said assembly comprising;

a sleeve of flexible insulative material into which said gripping means can be pulled;

and a terminal pin with excess length which is coupled at one end to said gripping means and which can extend through said sleeve when said terminal pin is inserted in said sleeve after said jaw formation is folded into and about the lead proximal end.

DESCRIPTION OF THE PREFERRED EMBODIMENTS

Figure 1:
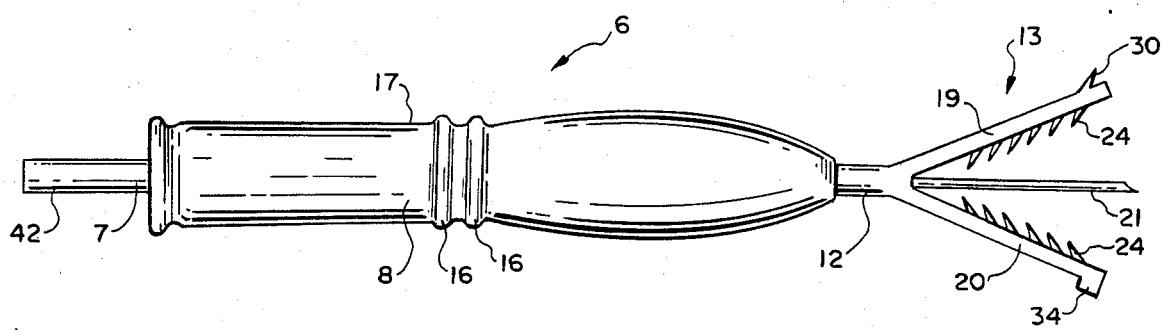
FIG. 1 is a side view of the quick connector/terminal electrode assembly of the present invention.

Referring now to the drawings in greater detail, there is illustrated in FIG. 1 a quick connector/terminal electrical assembly 6 constructed according to the teaching of the present invention for connection to a neural stimulator lead or a cardiac pacing lead.

The assembly 6 include stainless steel rod or rod-type extension 7, and an elastomeric tubular sleeve 8. The rod 7 is slidable in an axial direction in the sleeve 8.

The sleeve 8 has an internal axial or axially extending passageway 9 (FIG. 5) that extends the entire length thereof.

Figure 5:
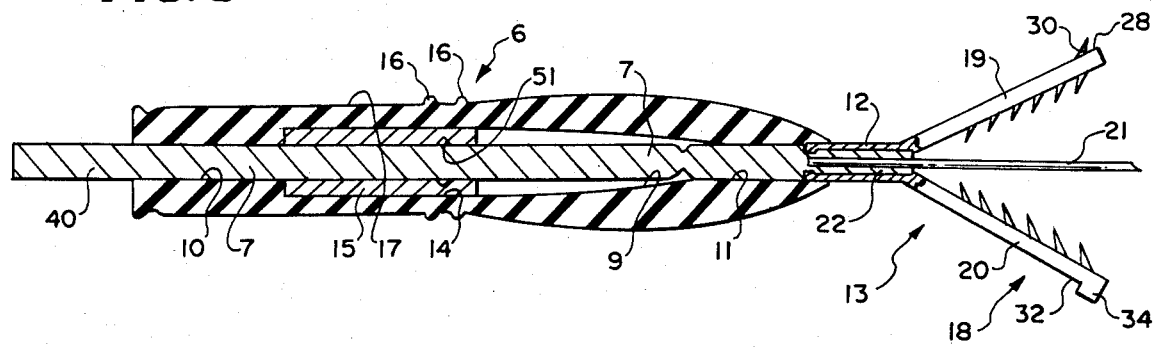
FIG. 5 is an axial sectional view of the quick connector/terminal electrode assembly shown in FIG. 1.

As shown in FIG. 5, opposite ends 10 and 11 of passageway 9 in sleeve 8 have common diameters which are sized to provide a fluid tight engagement with the rod 7 and a tube 12 of a jaw formation or gripper 13.

Between the sleeve ends 10 and 11 of the axial passageway 9 is an enlarged sleeve chamber or cavity 14 which receives a housing connector 15 as will be described in greater detail hereafter.

The assembly 6 is shown in FIG. 1 in the way in which it is "shipped" to a customer ready for use.

The sleeve 8 is preferably made from a silicone rubber of any suitable type that is non-reactive or inert to human body fluids and an extension (40 in FIG. 7) of the rod 7 exits from the sleeve 8 from the proximal end 10 of passageway 9.

Typically, the silicone rubber sleeve 8 has ridges 16 provided on an external surface 17 of the sleeve 8 to aid in the prevention of fluid entry into a socket in an implanted device (not shown).

The gripper 13 includes the tube 12 which has a bifurcated or split end 18 including spread apart arms on tube segments 19 and 20. The tube 12 is also fabricated of stainless steel. Extending through the center of the gripper 13 is a stainless steel stylet or guide wire 21 which is fixed in distal end 22 of rod 7.

Figure 3:
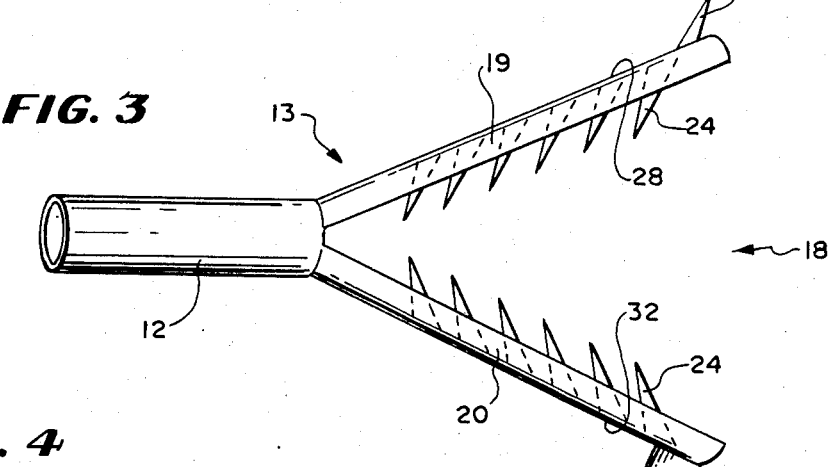
FIG. 3 is an enlarged perspective view of a tube of the rod and gripping assembly shown in FIG. 2 and shows diverging jaw-like tube segments carrying barbs.

Referring now to FIG. 3, the split tube end 18 has a plurality of barbs or teeth 24 extending inwardly from each arm or tube segments 19 and 20 and angularly toward the rod 7. As illustrated, and in one preferred embodiment, the gripper 13 is preferably stamped from a sheet of stainless steel of 0.008 inches in thickness. The tube 12 is then telescoped over a reduced-in-diameter stainless steel distal end 22 of the stainless steel extension or rod 7.

Alternatively, the gripper 13 can be fabricated from a stainless steel tube having an inner diameter approximately equal to the outer diameter of the distal end 22 of rod 7 and with a wall thickness of approximately 0.008 inches. The teeth or barbs 24 are mounted in the pair of jaw-like tube segments 19 and 20. These segments define the jaw formation or "gripper" 13. Alternatively, the barbs 24 can be punched out of arms 19 and 20.

Figure 4:
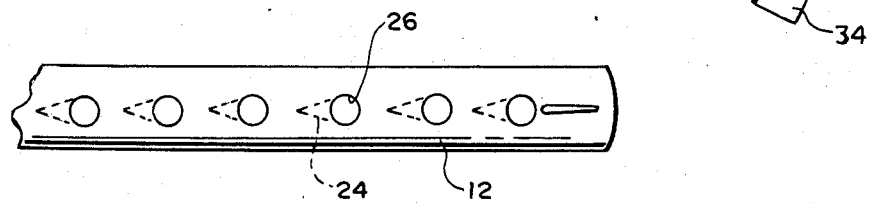
FIG. 4 is an enlarged fragmentary top plan view of one of the jaw-like tube segments shown in FIG. 3.

When the teeth or barbs 24 are assembled in the jaw-like tube segments 19 and 20 they then become an integral part thereof and a part of the gripper 13. In order to allow for ready assembly of the barbs 24 on the jaw-like segments 19 and 20, the segments 19 and 20 are provided with sockets 26 (FIG. 4) for receiving the barbs 24.

On an outer surface 28 of one jaw-like tube segment 19 is a protuberance 30 which projects in an opposite direction from the barbs 24 on the inner surface of the segment 19. On an outer surface 32 of the other jaw-like tube segment 20 is a stop 34. The function and operation of the protuberance 30 and the stop 34 will become evident from a description of the assembled relationship of the components described hereafter.

Figure 2:
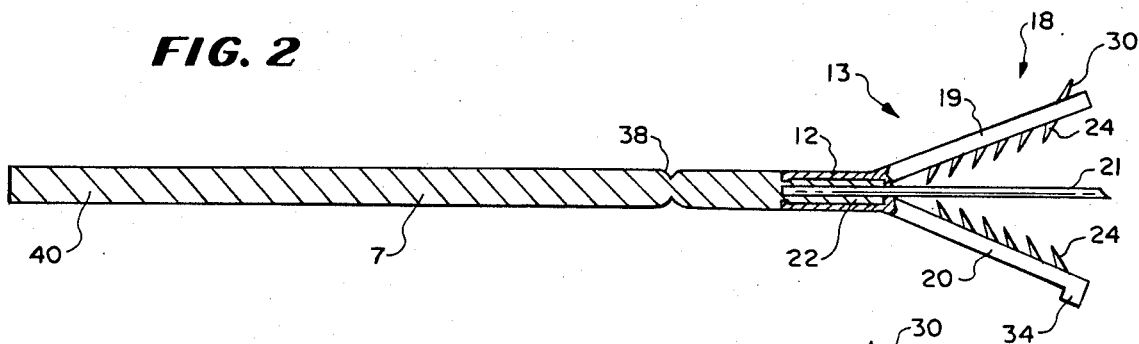
FIG. 2 is an axial cross-sectional view of a rod and gripper assembly of connector assembly shown in FIG. 1.

From an examination of the gripper 13 shown in FIGS. 2 and 3, it will be seen that the barbs 24 extend downwardly into an open space defined between the pair of jaw-like tube segments 19 and 20. The gripper 13, and more particularly its tubular end or tube 12 is spot welded in assembly with the distal end 22 of rod 7. Also, the guide wire or stylet 21 is spot welded to the distal end 22 of rod 7 after the stylet 21 is embedded in a socket 36 (FIGS. 6 and 7) in the distal end 22. It will of course be appreciated that the rod 7 is made of a single piece of stainless steel with a break-off groove 38 being provided to allow an excess portion of the rod 7 or extension, indicated at 40 in FIG. 7, to be broken at the groove 38 for eliminating the excess material once the components of the quick connector terminal electrode assembly 6 have been placed in assembled condition with a protruding end 42 of rod 7 forming an electrode or terminal pin 42.

The silicone rubber sleeve 12 is molded in assembly with the stainless steel connector housing or closer sleeve 15 in sleeve chamber 14 and a radially inwardly facing groove 51 is machined into an inner surface 52 (FIG. 7) of a distal end 53 of the closer sleeve 15.

Figure 6:
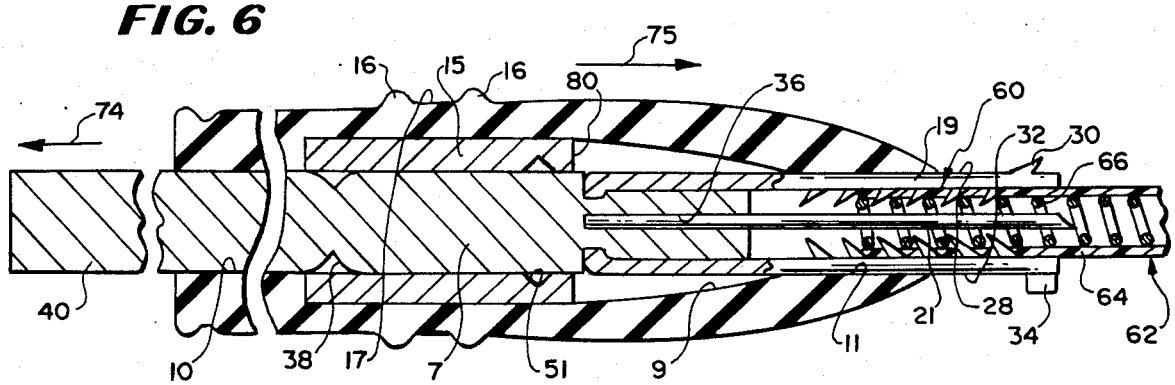
FIG. 6 is an enlarged fragmentary vertical/axial sectional view, similar to the view shown in FIG. 5, and shows arrows designating the way in which an elastomeric sleeve is moved relative to the rod and gripper assembly to close the jaw-like tube segments about the end of a medical electrical lead.

Referring now to the manner in which the various components of the assembly 6 are assembled, it will be observed in FIGS. 1, 2, 3 and 5 that the gripper or jaw formation 13 is in an open position. FIG. 6 illustrates the gripper 13 in a closed position. The closed position of the gripper 13 is brought about by folding or closing the arms 19 and 20 into and about a proximal end 60 of a medical electrical lead 62 to include a tubular insulation sheath 64 with a coiled conductor 66 within the sheath 4. Then relative axial movement of the rod 7 with respect to the sleeve 8 in the sleeve passageway 9 is caused by pulling end 40 of rod 7 as indicated by the oppositely pointing arrows 74 and 75 in FIG. 6.

Figure 7:
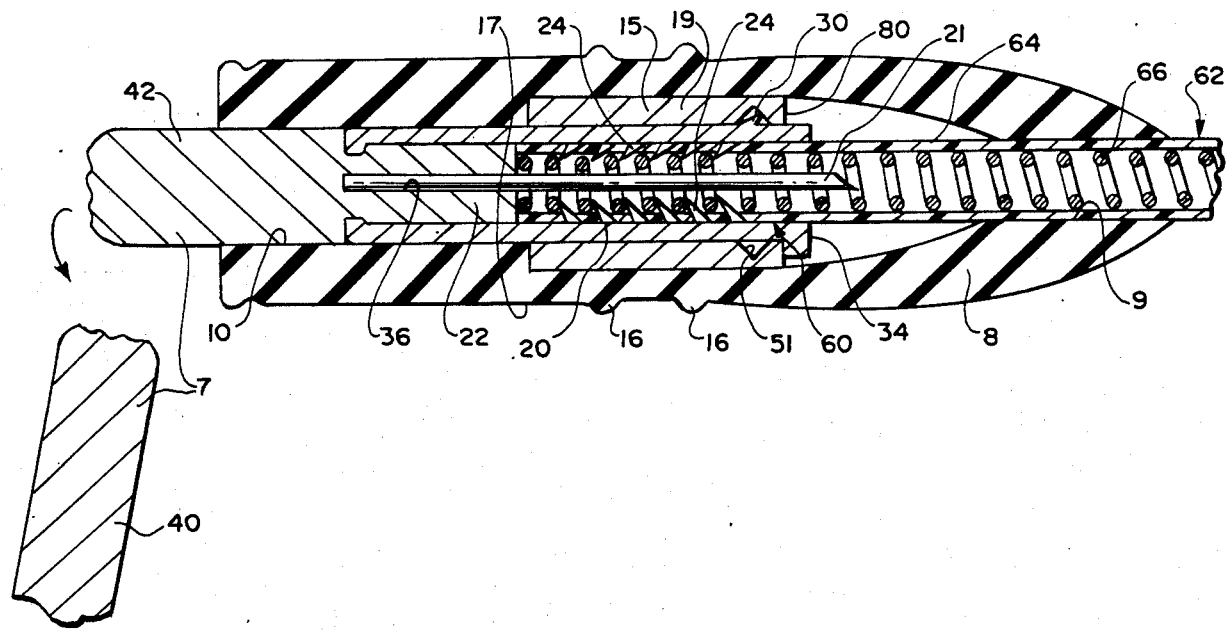
FIG. 7 is an enlarged fragmentary vertical/axial sectional view, similar to the view shown in FIG. 5, and shows the manner in which an end of the rod can be broken off at a break-off groove.

Stated another way, FIG. 6 illustrates the relationship of the components in a partially completed assembly of the connector terminal electrode assembly 6 with a medical lead 62 (FIGS. 6 and 7). The stylet or guide wire 21 is inserted in the center or lumen of coiled conductor 66 of the lead 62. The elastomer sleeve 8 of the assembly 6 is pushed toward the lead 62 and the rod 7 is pulled in an opposite direction in the passageway 8 as noted by the arrows 74 and 75.

After partial assembly has been completed as illustrated in FIG. 6, the connector/terminal electrode assembly 6 and the lead 62 are then finally assembled as illustrated in FIG. 7. This final assembly is completed by further relative movement of the stainless steel extension or rod 7 with respect to the silicone rubber sleeve 8 until the stop 34 engages against an annular outer end edge 80 of the stainless steel closer sleeve 15. By employing a stop 34 that is adapted to co-act and engage against the annular end edge 80 of the closer sleeve 15, the assembly 6 and the medical electrical lead 62 cannot be pulled through the silicone rubber sleeve 8. Further, the resilient bent-up tab or protuberance 30 engages in the radially inwardly facing groove 51 in the sleeve chamber 14. The presence of the resilient bent-up tab or protuberance 30 in the groove 51 prevents the terminal pin 42 of the rod 7 from being pulled out of the silicone rubber sleeve 8. With the diameter of the chamber 14 being greater than the radial outward extent of the tab 30, there is no interference with the sleeve 8 once the tab 30 clears the end 11 of sleeve passageway 8.

After the components have been assembled, then extension end 40 of the rod 7 is broken off and discarded as illustrated in FIG. 7 leaving just the terminal pin 42 adapted to be received in a pin receiving socket in a terminal electrode assembly receiving socket in an implanted device (not shown) such as a pacer.

In the use of the assembly 6, a physician cuts a lead 62 to a desired length or cuts off a connector/terminal electrical assembly from a lead 62. The cut proximal end 60 of the lead 62 is then placed over the guidewire 21 and pushed towards the tube 12 until the lead end 60 abuts the distal end 22 of the rod 7.

The two arms 19 and 20 of the gripper 13 are then squeezed together over the proximal end 60 so that the barbs 24 of the gripper 13 penetrate the sheath 64 of the lead 62. The elastomeric sleeve 8 is then pushed toward the lead 62 while the rod/terminal pin assembly 7 is pulled away from the lead 62. When the stop 34 on the gripper 13 abuts the end 80 of the closer sleeve 15 and the spring tab 30 is engaged in the groove 51 of the closer sleeve 15, the rod/terminal pin 7 cannot be pulled any further.

The terminal pin extension 42 is then broken off and discarded. When the silicone rubber sleeve 8 is in assembled position, the sleeve 8 snugly co-acts with the lead 62 and passageway ends 10 and 11 of passageway 9 provide a seal to preclude ingress of fluid when the connector/terminal electrode assembly 6 is implanted in the human body.

The distal end of the sleeve 8 which is an integral part of the rubber sleeve 8 exerts a continual pressure on the gripper 13 and the barbs 24 thus causing the barbs 24 to bite into the insulating sheath 64 of the lead 62. The coils of the coiled conductor 66 are also forced against the guidewire or stylet 21 thus assuring a good electrical contact therewith.

From the foregoing description it will be apparent that the connector assembly 6 of the present invention has a number of advantages some of which have been described above and others of which are inherent in the invention.

Also it will be understood from the foregoing description that modifications can be made to the quick connector assembly 6 of the present invention without departing from the teachings of the invention. Accordingly, the scope of the invention is only to be limited as necessitated by the accompanying claims.

I claim:

1. A quick connector for a neural stimulator lead or a cardiac pacing lead including: a rod-type extension, an elastomeric sleeve slidably mounted on said rod-type extension, a tube mounted in permanent assembly with one end of said rod-type extension, the tube being split at an outer end to provide a pair of jaw-like tube segments which extend in divergent relation when in an open position, each of the segments having a series of longitudinally spaced rearwardly extending barbs, a guide wire having an axially inner end co-axially embedded in said extension and an axially outer end projecting axially outwardly between said diverging jaw-like tube segments, and one end of a medical electrical lead being co-axially mounted over the guide wire, the lead having a tubular insulation sheath and axially spaced coils of a coiled conductor within the sheath and being positioned between the diverging jaw-like tube segments in radially disposed relation to the barbs, the rod-type extension and the elastomeric sleeve being axially movable relative to one another and operable to cause the diverging jaw-like tube segments to move radially inwardly into a closed position and to cause the barbs carried on the thus moved segments to become embedded in the coiled conductor for locking the medical electrical lead in fixed assembly with said rod-type extension.

2. The quick connector of claim 1 wherein said elastomeric sleeve is made of a silicone rubber and said rod-type extension is made of stainless steel.

3. The quick connector of claim 1 wherein said sleeve includes fluid seal means between said extension and said elastomeric sleeve for preventing fluid flow axially into the sleeve.

4. The quick connector of claim 1 wherein each diverging jaw-like tube segments has barb sockets for receiving said barbs and said barbs are mounted within said sockets, said barbs co-acting with the segments to provide means for forcing the coils against the guide wire thus assuring good electrical contact between said barbs, the coils and said guide wire.

5. The quick connector of claim 1 including means for exerting a continual pressure on said jaw-like tube segments and said barbs carried by said segments causing said barbs to bite into the insulative sheath to make good electrical contact with the coiled conductor.

6. The quick connector of claim 1 wherein said rod-type extension is made of stainless steel and has a break-off groove in its perimeter thus enabling an end portion of said extension remote from said guide wire to be broken at said break-off groove and detached from said extension leaving a stainless steel terminal pin projecting axially away from said elastomeric sleeve at its end remote from the medical electrical lead.

7. The quick connector of claim 1 including locking means which co-act between said rod-type extension and said sleeve for holding these components against relative axial movement in locked assembly whereby said barbs can be maintained embedded in the coiled conductor of the medical electrical lead.

8. The connector of claim 1 wherein said elastomeric sleeve has an axial sleeve passageway, a metallic closer sleeve is mounted internally of said axially passageway, locking means are provided which are engageable between said closer sleeve and one of said jaw-like tube segments upon said sleeve and said jaw-like tube segments being moved axially relative to each other for engaging said locking means and when engaged securing said sleeve and said jaw-like segments in a fixed position relative to one another.

9. The connector of claim 1 wherein said elastomeric sleeve has a stainless steel closer sleeve molded interiorly of the elastomeric sleeve, said closer sleeve being provided with a groove on an inner surface of a distal end thereof, and one of said jaw-like tube segments having a protuberance engageable in said groove for locking said tube and said extension attached thereto in a fixed position relative to said closer sleeve and said elastomeric sleeve.

10. The connector of claim 1 wherein said elastomeric sleeve has an axial sleeve passageway with opposite ends of the passageway having a common diameter and a chamber or cavity having a greater diameter than said passageway situated between the opposite ends of said passageway, a metallic closer sleeve being mounted in said chamber, and locking means being provided between said sleeve and one of said jaw-like tube segments for securing said sleeve in a fixed position relative to said rod-type extension when in an assembled condition.

11. The quick connector of claim 1 wherein said jaw-like tube segments are stamped from a sheet of stainless steel of 0.008 inches in thickness and are of such metallurgical characteristics as to enable said segments to be moved from a divergent open position to an essentially parallel closed position.

12. The quick connector of claim 11 wherein said segments have an outside diameter, approximating an outside diameter of said rod-type extension, thus enabling ready co-action between said sleeve and said segments and said rod-type extension to facilitate relative axial movement of these components when they are assembled.

13. A quick connector for a neural stimulator lead or a cardiac pacing lead including a rod-type extension, an elastomeric sleeve relatively inert to body fluids slidably mounted on said rod-type extension, said sleeve having an axially extending passageway and a chamber between its ends having a diameter greater than the diameter of said passageway, a tube fixed to one end of said rod-type extension, said tube being split at an outer end to provide a pair of jaw-like tube segments which extend in divergent relation when in an open position prior to assembly, each of said segments having a series of longitudinally spaced barbs, a guide wire having an axially extending inner end co-axially embedded in said extension and an axially extending outer end projecting axially outwardly between said diverging jaw-like tube segments, and a medical electrical lead proximal end co-axially mounted over said guide wire and having a tubular insulative sheath and axially spaced coils of a coiled conductor therein, the lead proximal end being positioned between said diverging jaw-like tube segments in radially disposed relation to said barbs, said rod-type extension and said elastomeric sleeve being axially movable relative to one another and operable to cause said diverging jaw-like tube segments to move radially inwardly into a closed position and to cause said barbs carried on the thus moved segments to become embedded in the coiled conductor for locking the medical electrical lead in fixed assembly with said rod-type extension as said tube is moved axially into said chamber.

14. The quick connector of claim 13 wherein said elastomeric sleeve is made of a silicone rubber, said rod-type extension is made of stainless steel, and fluid seal means are provided between said extension and said elastomeric sleeve for preventing fluid flow axially into said sleeve.

15. The quick connector of claim 13 wherein said diverging jaw-like tooth segments have barb sockets for receiving said barbs and said barbs are mounted within said sockets, said barbs co-acting with said segments to provide means for forcing the coiled conductor against said guide wire thus assuring good electrical contact of said guide wire and said barbs with the coils of the coiled conductor.

16. The quick connector of claim 13 including means in said sleeve for exerting a continual pressure on said jaw-like tube segments and said barbs carried by said segments causing said barbs to bite into the insulating sheath thus causing a good electrical contact of said barbs with coils of the coiled conductor.

17. The quick connector of claim 13 wherein said rod-type extension is made of stainless steel and has a break-off groove in its perimeter thus enabling an end portion of said extension remote from said guide wire to be broken at the break-off groove and detached from said extension leaving a stainless steel terminal pin projecting axially away from said elastomeric sleeve at its end remote from the medical electrical lead.

18. The quick connector of claim 13 including locking means co-acting between said rod-type extension and said sleeve for holding these components against relative axial movement in locked assembly whereby said barbs are maintained embedded in the coiled conductor and the sheath of the lead.

19. The quick connector of claim 13 wherein said jaw-like tube segments are stamped from a sheet of stainless steel of 0.008 inches in thickness and have such metallurgical characteristics as to enable said segments to be moved from a divergent open position to an essentially parallel closed position.

20. The quick connector of claim 19 wherein said segments have an outside diameter, approximating an outside diameter of said rod-type extension, which enables ready co-action between said sleeve and said segments and said rod-type extension to facilitate relative axial movement of these components when they are assembled.

21. A method for forming a terminal electrode assembly at the proximal end of a medical electrical lead of the type comprising a tubular sheath and a coiled conductor within the sheath, said method comprising:
  providing gripping means including a jaw formation with teeth capable of piercing the sheath and capable of making electrical connection with the coiled conductor;
  providing a sleeve made of a flexible, insulative material into which said gripping means can be pulled;
  providing a terminal pin with excess length which is coupled at one end to said gripping means and which can extend through said sleeve;
  placing said gripping means over the proximal end of the medical electrical lead;
  folding said jaw formation into and about the proximal end of the lead;

inserting said terminal pin into and through the sleeve;

pulling said terminal pin through a major portion of said sleeve to pull said gripping means and the lead proximal end into the sleeve.

22. The method of claim 21 including the step of fixing said gripping means in said sleeve.

23. The method of claim 21 including the step of cutting off any excess length of terminal pin to provide a desired terminal pin length.

24. The method of claim 23 including the step of providing a weakened area in said terminal pin to facilitate breaking off of the excess length of said terminal pin at the weakened area.

25. A terminal electrode assembly for connecting to a proximal end of a medical electrical lead of the type comprising a tubular sheath and a coiled conductor within the sheath, said assembly comprising;

gripping means including a jaw formation having teeth capable of piercing the sheath to make electrical contact with the coiled conductor;

a sleeve of flexible insulative material into which said gripping means can be pulled;

and a terminal pin with excess length which is coupled at one end to said gripping means and which can extend through said sleeve when said terminal pin is inserted in said sleeve after said jaw formation is folded into and about the lead proximal end.

26. The terminal electrode assembly of claim 25 including means in said sleeve for fixing said gripping means in said sleeve after a major portion of said terminal pin has been pulled through said sleeve.

27. The terminal electrode assembly of claim 26 wherein said terminal pin has a weakened area to facilitate breaking off of the excess length of said terminal pin at said weakened area after a major portion of said terminal pin has been pulled through said sleeve.

28. The assembly of claim 27 including means for holding the folded in assembly of said arms gripping the proximal end of the lead within said cavity.

29. A quick connector assembly for creating and securing a terminal electrode assembly to the proximal end of a medical electrical lead, such as a pacing lead or a neural stimulator lead, said connector/terminal electrode assembly comprising a sleeve of insulative flexible material having a distal end, a proximal end, a cavity therein and first and second bores, smaller-in-cross-section than said cavity, in the distal and proximal ends respectively of said sleeve, a rod received within said bores and having a distal end and a proximal end extending out of said second bore, a metal sleeve having a proximal end fixed to the distal end of said rod and a bifurcated distal end which includes a first arm and a second arm and which extends out of said first bore, said arms initially being spread apart, each arm having projections facing each other and being capable of being folded into a proximal end of a lead having an outer insulation sheath and a coiled conductor within the sheath such that the projections pierce the sheath and make electrical contact with the coiled conductor, said rod being inserted into said sleeve through said first bore and being capable of being pulled through said second bore.

* * * * *

UNITED STATES PATENT AND TRADEMARK OFFICE
CERTIFICATE OF CORRECTION

PATENT NO. : 4,614,395

DATED : September 30, 1986

INVENTOR(S) : Charles A. Peers-Trevarton

It is certified that error appears in the above-identified patent and that said Letters Patent is hereby corrected as shown below:

Column 4, line 60, "4" should read -- 64 --.

Column 7, line 43, "including a" should read -- including:a --.

Signed and Sealed this

Seventeenth Day of February, 1987

Attest:

DONALD J. QUIGG

Attesting Officer     Commissioner of Patents and Trademarks